United States Patent [19]

Armenta et al.

[11] Patent Number: 4,578,350

[45] Date of Patent: Mar. 25, 1986

[54] IMMUNOASSAYS EMPLOYING PROTECTED LABELS

[75] Inventors: Richard D. Armenta, Mountain View; Ian Gibbons, Menlo Park, both of Calif.

[73] Assignee: Syntex (U.S.A.) Inc., Palo Alto, Calif.

[21] Appl. No.: 535,452

[22] Filed: Sep. 23, 1983

[51] Int. Cl.$^4$ .................... G01N 53/00; C12N 9/96
[52] U.S. Cl. ........................ 435/7; 435/188; 436/801; 436/537
[58] Field of Search ........... 435/7, 177, 178, 188; 436/537, 532, 801

[56] References Cited

U.S. PATENT DOCUMENTS 4,275,149  6/1981  Litman et al. ............... 435/7
4,423,143  12/1983  Rubenstein et al. .......... 435/7

FOREIGN PATENT DOCUMENTS 2019562  10/1979  United Kingdom .

OTHER PUBLICATIONS

Thierault et al., Clin. Chem. 23/11: 2142–2144 (1977).
Fortier et al., Clin. Chem. 25/8: 1466–1469 (1979).
Conradie et al., S. Afr. Med. J., 57: 282–287 (1980).
Pagé et al., Scand. J. Clin. Lab. Invest., 40: 641–645 (1980).
Anderson et al., Clin. Chem. Acta., 116: 405–408 (1981).
Linpisarn et al., Ann. Clin. Biochem., 18: 48–53 (1981).
Addison et al., J. Clin. Path., 25, 326–329 (1972).
Miles et al., Analytical Biochemistry, 61, 209–224 (1974).
Porter, J. Lab. Clin. Med., 83, 147–152 (1974).
Carmel et al., Analytical Biochemistry, 85, 499–505 (1978).
Laurell, Analytical Biochemistry, 15, 45–52 (1966).
Kitagawa et al., J. Biochem., 79, 233–236 (1976).

*Primary Examiner*—Christine M. Nucker
*Assistant Examiner*—Shawn P. Foley
*Attorney, Agent, or Firm*—Theodore J. Leitereg; Carole F. Barrett

[57] ABSTRACT

An improved immunoassay for determining the presence of an analyte in a serum sample and conjugates therefor are described. The known method comprises combining the sample with a conjugate of the analyte and an enzyme and with a receptor for analyte, and determining the presence of analyte in the sample from the effect that the sample has on the enzymatic activity when compared to the enzymatic activity in the absence of analyte or in the presence of known amounts of analyte. The present invention resides in the conjugation to the enzyme label of a label protectant which allows modulation of the enzymatic activity to occur and minimizes background interference between the enzyme label and the sample, which would alter the enzymatic activity.

19 Claims, No Drawings

IMMUNOASSAYS EMPLOYING PROTECTED LABELS

BACKGROUND OF THE INVENTION

1. Field of the Invention

Enzyme immunoassay methods are known for the determination of the presence in a sample of an analyte. The known method comprises determining the effect that the sample containing the analyte has on the binding between a conjugate of the analyte (ligand) and an enzyme and a receptor for the analyte. When the conjugate and the receptor bind, a modulation of the enzymatic activity occurs. The presence of analyte in the sample can be determined from the effect that the analyte has on the modulation of the enzymatic activity when compared to that obtained in the absence of analyte or in the presence of known amounts of analyte.

In some cases, the number of molecules of analyte to the number of molecules of enzyme label will be greater than one and in other cases, the number of molecules of enzyme label to number of molecules of analyte in the conjugate will be greater than one. The latter situation may arise where the analyte has a high molecular weight, either because it is a high molecular weight material or because of aggregation of lower molecular weight materials producing a material with a high molecular weight. For example, there are high molecular weight proteins which have drawn increasing attention in recent years as knowledge of their functions and their significance in medical diagnosis has grown. The need for sensitive and efficient assays for these proteins has likewise grown. To this end, various immunoassay techniques have been applied.

The large size of these proteins, however, has heretofore limited the number of immunoassays which could provide a detectable signal. In particular, enzyme immunoassays have been limited to cumbersome procedures involving progressive binding reactions and phase separation. This is a serious limitation since enzyme immunoassays have the advantage of permitting spectrophotometric determinations and the potential of offering high sensitivity due to rapid substrate turnover rates which amplify the signal.

For a large number of analytes, the concentration range of interest will fall between 100 micrograms to 1 pg per ml. For many analytes, the concentration range of interest will vary from about twofold to one hundred fold so that a quantitative determination will require the ability to distinguish small differences in the concentration of the analyte in the assay medium. Immunoassays are predicated on detecting the complexation between the ligand and receptor. The lower the concentration of analyte, the fewer the number of complexes which are formed.

One problem which may arise in enzyme immunoassays is background interference which tends to obscure the modulation of enzymatic activity normally causing a diminution of enzyme activity. Immunoassays of enhanced sensitivity, therefore, are needed particularly those which will permit the determination of large proteins in a simple and efficient manner.

2. Description of the Prior Art

A novel biological assay method for determining the presence of a specific organic material by employing a modified enzyme for amplification is disclosed in U.S. Pat. No. 3,817,837. In U.S. Pat. No. 4,267,270, there is described a method for the determination of antigens and antibodies using site deactivating media.

Solid phase sandwich enzyme immunoassays for ferritin, a protein with a molecular weight of approximately 450,000 daltons, are disclosed in Therialt, et al., *Clin. Chem.*, 23/11:2142–2144 (1977); Fortier, et al., *Clin. Chem.*, 25/8:1466–1469 (1979); Conrade, et al., *S. Afr. Med. J.*, 57:282–287 (1980); Paige, et al., *Scand. J. Clin. Lab. Invest.*, 40:641–645 (1980); Anderson, et al., *Clin. Kim. Acta.*, 116:405–408 (1981); and Linpisarn, et al., *Am. Clin. Biochem.*, 18:48–53 (1981).

Immunoassays for ferritin which do not involve enzymes include two site immunoradiometric assays as disclosed in Addison, et al., *J. Clin Pathol.*, 25:326–329 (1972) and Miles, et al., *Anal. Biochem.*, 61:209–224 (1974). Competitive radioimmunoassays as disclosed in Porter, *J. Lab. Clin. Med.*, 83:147–152 (1974) and electroimmunoassays as disclosed in Carmel, et al., *Anal. Biochem.*, 85:499–505 (1978) and Laurell, *Anal. Biochem.*, 15:45–52 (1966). Copending application U.S. Ser. No. 258,848 filed Apr. 29, 1981, discloses conjugates of a ligand and $\beta$-D-galactosidase for enzyme immunoassays.

SUMMARY OF THE INVENTION

We have discovered that, in an enzyme immunoassay of a sample containing an analyte, background interference arises from interaction between the enzyme label and a component, or components, of the sample other than analyte. The interaction between the enzyme and such component appears to be specific in that such component recognizes a particular spatial and polar organization of the enzyme. We further have discovered that this background interference can be minimized by conjugating a label protectant, normally a protein, to the enzyme label. The invention includes a conjugate comprising (1) a ligand, (2) an enzyme label capable of providing a detectable signal in an immunoassay, wherein the binding of the labelled ligand with a receptor for ligand results in a modulation of the signal, and (3) a label protectant which allows modulation of the signal to occur when the labeled ligand and receptor combine and minimizes the reduction in enzyme activity due to components in the sample other than analyte.

In the known method the effect that the analyte has on the binding between a ligand-enzyme conjugate, wherein the ligand is normally analyte, and a receptor for the ligand is determined. When the conjugate and receptor bind or complex, a modulation of the signal produced by the label occurs. The presence of analyte in the sample can be determined from the effect that the analyte has on the modulation of the signal when compared to that obtained in the absence of analyte or in the presence of known amounts of analyte. The effect results from the analyte's affinity for the receptor. As mentioned above, the present invention resides in the conjugation to the label of a label protectant which allows modulation of the signal to occur when the ligand-enzyme conjugate and receptor for ligand bind and minimizes the reduction in enzyme activity due to components of the sample other than analyte, which would tend to obscure the modulated signal.

The improved assay provides for a convenient method for detecting and measuring a wide variety of analytes in a simple, efficient, and reproducible manner. The invention finds particular application to enzyme immunoassays wherein the analyte is a high molecular weight protein such as ferritin and the label is an enzyme requiring a macromolecular substrate for optimal signal production.

DESCRIPTION OF THE SPECIFIC EMBODIMENTS

Before further describing the invention, a number of terms will be defined.

Analyte—A compound or composition to be measured, which may be a ligand, which is mono- or polyepitopic, usually antigenic or haptenic, a single or plurality of compounds which share at least one common epitopic or determinate site or a receptor.

Ligand—Any organic compound for which a receptor naturally exists or can be prepared.

Receptor (anti-ligand)—Any compound or composition capable of recognizing a particular spatial and polar organization of a molecule that is epitopic or a determinate site. Illustrative receptors include naturally occurring receptors, i.e., throxine binding globulin, antibodies, enzymes, Fab fragments, lectins, nucleic acids, and the like.

Ligand analog—A modified ligand which can compete with analogous ligand for a receptor, the modification providing means to join a ligand analog to another molecule. The ligand analog will usually differ from the ligand by more than replacement with a bond which links the ligand analog to a hub or label, but need not.

Poly(ligand-analog)—A plurality of ligand or ligand analogs covalently joined together, normally to a hub nucleus. The hub nucleus is a poly-functional material, normally polymeric, usually having a plurality of functional groups, i.e., hydroxy, amino, mercapto, ethylenic, etc. as sites for linking. The hub nucleus is normally water soluble or at least dispersible and will usually be about 35,000 daltons but generally not exceeding about 600,000 daltons. Illustrative hub nuclei include polysaccharides, polypeptides, including proteins, nucleic acids, ion exchange resins and the like.

Label—The label may be any molecule conjugated to another molecule where each of the molecules has had or can have had a prior discrete existence. For the most part, labels will be compounds which are conjugated to a ligand and which are capable of producing a detectable signal.

Label protectant—The label protectant is a proteinaceous compound, such as a polypeptide or mucopolysaccharide, having a molecular weight of about 20,000–100,000 daltons, preferably, 50,000–70,000 daltons and, preferably, a charge characteristic similar to the ligand-enzyme conjugate such that the binding between the labeled ligand and the receptor remains substantially unaltered. It is preferred that the label protectant not be a compound having a receptor which would be expected to be an endogenous component of serum. The label protectant when conjugated to the label, allows modulation of signal resulting from binding of the labeled ligand and the receptor to occur and minimizes the reduction of enzyme activity due to endogenous components of the sample other than analyte, which reduction in enzyme activity would obscure the modulated signal.

Molecular ratio—The ratio of the number of molecules of label to the number of molecules of ligand to which the label is attached.

As mentioned earlier, the invention includes conjugates comprising (1) a ligand which generally corresponds to an analyte, (2) an enzyme label capable of providing a detectable signal in an immunoassay wherein the binding of the labeled ligand with a receptor for ligand results in a modulation of the signal produced, and (3) a label protectant.

In the known enzyme immunoassay methods, generally, the ligands are characterized by being monoepitopic or polyepitopic. The polyepitopic ligands will normally be haptenic or antigenic, e.g., poly(amino acids) i.e., polypeptides and proteins, polysaccharides, and aggregates and combinations thereof. For the most part, the polyepitopic ligands employed in the subject invention will have a molecular weight of at least about 5,000, more usually at least about 10,000. In the poly(amino acid) category, the poly(amino acids) of interest will generally be from about 1,000 to 5,000,000 molecular weight, more usually about from 5,000 to 1,000,000 molecular weight. The invention finds particular application in enzyme immunoassays for high molecular weight proteins, i.e., proteins of molecular weight of about 250,000–2,000,000 daltons, preferably of about 350,000–1,000,000 daltons, more preferably between about 400,000 and about 600,000 daltons. With high molecular weight proteins the conjugate will usually consist of a single ligand bonded on the average to at least one label, depending upon the size of the ligand. Ligands with a molecular weight of 250,000–2,000,000 daltons will preferably contain on the average from about 2 to about 10 labels per ligand. Ligands with a molecular weight of about 400,000–600,000 daltons will preferably contain on the average of about 3 to 5 labels per ligand. Exemplary of high molecular weight proteins is ferritin.

Receptors will be macromolecules which have sites which recognize specific structures. Those of greatest interest are proteins, particularly antibodies produced primarily by introducing an immunogenic substance into the bloodstream of a living animal or by biotechnology. A description of antibodies useful in the present invention is found in U.S. Pat. No. 3,817,837 at columns 36–37 (incorporated herein by reference).

Conjugation of the labels to the ligand is achieved through linking group providing a covalent connection. Preferably, the linking group is inert. The term "inert" is used to signify that the linking group will remain substantially unchanged during the binding reactions which take place in the assay. Conjugates of ligands and enzymes are described in U.S. Pat. No. 3,817,837, particularly at column 6-column 36, the disclosure of which is incorporated herein by reference. Conjugates of receptors and labels are described in U.S. Pat. No. 4,208,479 the disclosure of which is incorporated herein by reference.

The invention is next described in detail employing, for the sake of illustration and not by way of limitation, the situation wherein the analyte is ferritin, the ligand-enzyme conjugate is ferritin/$\beta$-galactosidase, and the receptor for ligand is antibody for ferritin (anti-ferritin). In the present invention the ferritin/$\beta$-galactosidase conjugate is further conjugated to an enzyme protectant. Tne enzyme protectant may be a proteinaceous compound such as, for example, mucopolysaccharide, or the like, having a molecular weight of less than about 100,000 daltons, preferably less than about 70,000 daltons, and, preferably, a charge characteristic similar to that for the labeled ligand. The labeled ligand will have a particular electronic (or charge) character, which influences the binding between the receptor and the labeled ligand. The label protectant should have an electronic (or charge) character substantially similar to the labeled ligand so that the binding between labeled ligand and receptor remains substantially unaltered.

The label protectant may be selected from the following: protamines, histones, albumins, and globulins, globlins. Other polymeric materials of interest are mucopolysaccharides, oligosaccharides, and polysaccharides. The preferred proteins for use as the label protectant are animal derived plasma proteins such as albumins, gamma globulins and the like.

The label protectant will have a great diversity of functionalities which may be present. In addition, the functionalities which are present may be modified so as to form a different functionality. For example, keto to hydroxy or olefin to aldehyde or carboxylic acid. A wide variety of different types of functionalities have been developed specifically for linking various compounds to proteins.

The enzyme protectant may be bound to the $\beta$-galactosidase in a variety of ways. In a preferred embodiment, the enzyme protectant is covalently conjugated to the enzyme in the same or similar manner as the $\beta$-galactosidase is conjugated to the ferritin. The enzyme protectant is normally bonded either directly to the enzyme by a single or a double bond or preferably through a linking group. It is important that the enzyme protectant be conjugated to the $\beta$-galactosidase and not to tne ferritin. Consequently, prior to conjugation of the enzyme and enzyme protectant, any functional group on the ferritin, equivalent to the particular enzyme functional group that will be used for conjugation, must be rendered inactive. This may be accomplished, for example, by reacting such functional groups on the ferritin with a blocking group. The functional groups which may be present in the enzyme for linking are thiol, amino (including guanidino), hydroxy, and carboxy. In addition, for some enzymes activated aromatic groups or imidazole may also serve as a site for linking. The preferred functional group for linking is thiol.

Where a linking group is employed for bonding the enzyme protectant to the enzyme, it will be the more frequent procedure first to bond the linking group to the enzyme protectant to provide an active site for bonding to the enzyme. This may be achieved in a single step or may require a plurality of synthetic steps including blocking and unblocking the active groups on the enzyme protectant other than the one involved in providing the linking group. The linking groups which are reported hereafter are solely concerned with the bridge bonding the enzyme and the enzyme protectant.

The linking group (excluding the atoms derived from tne enzyme protectant and the enzyme), when other than a direct bond is involved, will be of from about one to 30 atoms—carbon, hydrogen, nitrogen, oxygen, phosphorous, and sulfur—more usually 4 to 20 atoms.

Preferably, the linking group will normally be of from 0 to 14 carbon atoms, usually from 1 to 8 carbon atoms and from 1 to 8 heteroatoms, and frequently of from 1 to 8 carbon atoms and from 1 to 4 heteroatoms, which are oxygen, sulfur and nitrogen, more usually oxygen and nitrogen. The preferred functionalities present in the linking group for linking to the enzyme protectant are non-oxocarbonyl (substituted carbonyl or thiocarbonyl) and oxy.

As mentioned above, the preferred linking group (after linking to the enzyme protectant) provides a covalent connnection to the enzyme portion of the enzyme-bound ligand. The preferred functionality is an activated olefin group (usually a carbonyl activated olefin group), i.e., an olefin group activated for reaction with a functionality on the enzyme, particularly a thiol group. Exemplary linking groups are maleimidyl, e.g., N-(4-carboxycyclohexylmethyl)maleimide, N-(m-benzoyl)maleimide, and the like.

The reaction conditions employed in the formation of the conjugate between the $\beta$-galactosidase and the enzyme protectant will normally be similar to the conditions used in forming the conjugate between the enzyme and the ligand. The reaction mixture during conjugation will normally be brought to a pH in the range of about 5-10, more usually in the range of about 6-9. Various buffers may be used such as phosphate, carbonate, Tris, and the like. An aqueous solvent will normally be used and up to about 40 wt % of an oxyethylene alcohol or ether having from 1 to 3 oxyethylene units may be present. Particularly useful is carbitol. The temperatures will normally range from about $-5°$ C. to about 40° C., usually from about 0° C. to about 25° C.

We have found that, with respect to a ligand which is a high molecular weight protein having a negative charge and an enzyme protectant such as albumin which also has a negative charge, it is desirable to carry out the conjugation in a medium of ionic strenth in the range of about 0.5 to 2, preferably about 1.

In preparing conjugates of ferritin and $\beta$-galactosidase, it is desirable that the enzyme retain on the average at least about 10%, preferably at least about 40%, of its original enzyme activity. Furthermore, at least one epitopic site on the ferritin in the conjugate is left accessible to a macromolecular receptor. The preparation of the (ferritin/$\beta$-galactosidase)-(enzyme protectant) conjugate will generally be subject to the same criteria with the exception that no more than an additional 25% reduction of the original enzyme activity over that for the ferritin/$\beta$-galactosidase conjugate is desirable. The conjugation of enzyme-protectant and ferritin/$\beta$-galactosidase conjugate can be monitored by well-known techniques to ascertain the reduction in enzyme activity.

The (ferritin/$\beta$-galactosidase)-(enzyme protectant) conjugate is prepared in such a way that the binding of a receptor to the ferritin portion causes a reduction of at least about 10%, preferably about 30%, and more preferably at least about 50%, in the activity of the enzyme. As an optional variation, a second receptor can be introduced into the assay medium with specificity for the first receptor or for the complex formed by the binding of the first receptor to the conjugate. Use of the second receptor can increase overall enzyme inhibition or reduce the amount of agents so that the same degree of inhibition can be achieved using a lesser amount of the first receptor.

The amount of enzyme protectant to be conjugated to the enzyme will vary depending upon the nature of the enzyme and the protectant and the amount of protection which is desired for the enzyme. The number of enzyme protectants conjugated to the enzyme of the ligand-enzyme conjugate will be such that there will be a substantial reduction in the background interference due to specific and non-specific interactions between the enzyme and components of the sample other than analyte. However, a sufficient enzyme activity will be retained to meet the requirements mentioned above. In general, conjugation of at least about one enzyme protectant per 40,000 molecular weight of enzyme, preferably at least about one enzyme protectant per 20,000 molecular weight of enzyme, is satisfactory. A sufficient number of active sites for the enzyme must remain such that binding of the ligand portion of the conjugate to a receptor will result in a sufficient modulation of the enzymatic activity to provide a detectable signal. Normally, the active sites remaining after conjugation of the ligand-enzyme to the enzyme protectant should be in the area where binding will take place between the receptor and the ligand.

The compounds of the invention have the formula:

$$J_p(XY)_n(XZ)_m \qquad (I)$$

wherein:

J is a monoepitopic ligand or a polyepitopic ligand comprising polypeptides and proteins, polysaccharides, and aggregates thereof having a molecular weight of at least about 5,000, more usually at least about 10,000, and no more than about 5,000,000. Generally, the molecular weight will be about 20,000 to 2,000,000;

the two Xs may be the same or different;

X is a bond or a linking group of about 1 to 30 atoms, comprising carbon, hydrogen, nitrogen, oxygen, and sulfur, usually 4–20 atoms; preferably of from 0–14 carbon atoms, usually 1–8 carbon atoms, and from 1 to 8 heteroatoms; frequently of from 1 to 8 carbon atoms and from 1 to 4 heteroatoms, which are oxygen, sulfur and nitrogen, more usually oxygen and nitrogen;

Y is a compound capable of producing a detectable signal in an immunoassay, usually an enzyme, preferably β-galactosidase;

p is a number between 1 and the molecular weight of Y divided by 2000, usually between about 2 to about 40, being 1 when n is greater than 1;

n is a number between about 1 and about 10, usually about 2 and about 10, being 1 when p is greater than 1;

Z is a proteinaceous compound, usually a protein, or a mucopolysaccharide, having a molecular weight of about 20,000–100,000 daltons, preferably about 50,000–70,000 daltons, and a charge characteristic similar to that for JXY, preferably an animal derived plasma protein;

m is a number at least 1 per Y group, usually at least 1 per 40,000 molecular weight of the Y group, preferably at least 1 per 20,000 molecular weight of the Y group.

Some of the compounds of the invention, which are preferred, have the formula:

$$J'(XY)_{n'}(X'Z')_m \qquad (II)$$

wherein:

X and m have been defined above;

J' is a protein having a molecular weight of about 250,000–2,000,000 daltons, usually about 350,000–2,000,000, preferably about 350,000–1,000,000, more preferably 400,000–600,000;

X' is a linking group which is a bifunctional radical having from 0–14 carbon atoms, usually from 1 to 8 carbon atoms and from 1 to 8 heteroatoms; frequently from 1 to 8 carbon atoms and from 1 to 4 heteroatoms, which are oxygen, sulfur, and nitrogen, wherein the functionality linked to Y' is derived from non-oxo-carbonyl (including the nitrogen imino and thio-carbonyl analogs thereof) or oxy, and the functionality linked to Z' is derived from an olefin group activated for reaction with a functionality on Z', usually derived from a carbonyl-activated olefin group, activated for reaction with a thiol group, such as maleimidyl, preferred X' being derived from N-(4-carboxycyclohexylmethyl)maleimide and N-(m-benzoyl)maleimide with X' being, respectively, N-(4-carboxycyclohexylmethyl)-α-succinimidyl and N-(m-benzoyl)-α-succinimidyl;

Y' is an enzyme;

n' is a number between about 1 and about 10; usually about 2 and about 10;

Z' is an animal derived plasma protein having a molecular weight of about 50,000–70,000 daltons; and m has been defined above.

Particularly preferred compounds of the invention have the formula:

$$J''[(CO)RWSY''S]_{n''}[WR(CO)Z'']_{m'} \qquad (III)$$

wherein:

J'' is a protein having a molecular weight of about 400,000–600,000 daltons, e.g., ferritin;

R is an aliphatic (including alicyclic) linking group, normally saturated aliphatic of from 1 to 12 carbon atoms, preferably 5 to 10 carbon atoms, more preferably 7 carbon atoms;

W is derived from an activated olefin group having from 4 to 10 atoms, usually 6–8 atoms, which may be carbon, chalcogen of atomic number 8 to 16 (oxygen and sulfur) and nitrogen; usually derived from a carbonyl (including thiocarbonyl) activated olefin group having 6 to 8 atoms including 3 to 4 carbon atoms and at least one carbonyl group bound to the olefin group wherein nitrogen, if present, is amido; usually derived from maleimidyl being therefore α-succinimidyl such as N-(4-carboxycyclohexylemthyl)-α-succinimidyl and N-(m-benzoyl)-α-succinimidyl;

SY''S is β-galactosidase;

n'' is 3 to 4;

Z'' is an animal derived plasma protein having a molecular weight of about 50,000–70,000 daltons; and m' is m, which has been defined above.

The invention finds particular use for enzyme immunoassays wherein the enzyme, after its conjugation to a ligand, contains at least one free thiol group and wherein a macromolecular substrate is employed to enhance the detectable signal. Preferred macromolecular substrates are polysaccharide macromolecular supports to which is attached an enzyme substrate. For example, for the enzyme β-galactosidase the macromolecular substrate may be a galactosidyl ether of nitrophenol or umbelliferone. Exemplary substrates in the latter instance are disclosed in Skold, U.S. Pat. No. 4,268,663, issued May 19, 1981, incorporated herein by reference in its entirety, and Madhare et al., *Enzyme*, 25:127–131 (1980). Various other β-galactoside derivatives, exemplified in the literature, can serve as substrates.

When the enzyme employed in the conjugate contains free thiol groups which are used for conjugation, it is generally preferred tnat the linking group contain, as one functionality, an activated olefin group for combining with the free thiol group of the enzyme. The activated olefin group is usually a carbonyl activated olefin group with the preferred linking functionality being maleimidyl, e.g., N-(4-carboxycyclohexylmethyl)maleimide and N-(m-benzoyl)maleimide.

For the conjugation of such enzymes to protein (ligand, receptor or label protectant) it is desirable to block any available thiol groups on the protein molecule. This will assure that only thiol groups on the enzyme will bind to the functionality on the linking group during formation of the conjugate. As a blocking agent one may use an agent containing a functionality reactive only to thiol groups, such as an olefin group activated for reaction with a thiol group, generally a carbonyl-activated olefin group, e.g., N-ethyl maleimide.

EXAMPLES

The invention is further demonstrated by the following illustrative examples.

All temperatures are in centigrade. All parts and percents not otherwise indicated are by weight, except for mixtures of liquids, which are by volume. All solutions are aqueous solutions unless otherwise indicated. The following abbreviations are used:

h—hour; NEM—N-ethyl maleimide; MBSE—m-maleimidobenzoyl-N-hydroxysuccinimide ester [N-hydroxysuccinimide ester of N-(m-benzoyl)maleimide]; DTNB—5,5'-dithiobis-(2-nitrobenzoic acid); EDTA—ethylenediamine tetraacetic acid, disodium salt; DONPG—dextran linked o-nitrophenylgalactoside (prepared according to the teaching of U.S. Pat. No. 4,268,663); RIA—radioimmunoassay; RSA—rabbit serum albumin; PBS, $N_3$,Mg—phosphate buffered saline, azide, magnesium; $PO_4(Na+)$—combination of mono and disodium phosphate; DUG—dextran linked umbelliferone $\beta$-galactoside (prepared from dextran having a moleculr weight of 40,000 and about 14% of its amino groups modified with umbelliferone $\beta$-galactoside groups; EtOH-ethanol; EDCI-ethyldimethylaminopropylcarbodiimide; DTE-dithioerythritol; and SMCC-succinimidyl 4-(N-maleimidomethyl)cyclohexane-1-carboxylate [N-hydroxysuccinimide ester of N-(4-carboxycyclohexylmethyl)malimide].

Source of materials was as follows:
MBSE—Pierce 22310; NEM—Sigma 3876; DMF—Mallincrodt DLRE; DTNB—Sigma D8130; EDTA—Sigma 49C-0507; and SMCC—Pierce 50908.

EXAMPLE I

Preparation of Ferritin/$\beta$-Galactosidase/Albumin Conjugate a. Modification of ferritin sulfhydryls with NEM:
Purified human ferritin at 5 mg/ml in 0.05M phosphate buffer at pH 7.0 was combined with 10 $\mu$l of a 10 mM solution of DTE. The resulting mixture was stirred at room temperature for one hour, then combined with 30 $\mu$l of a DMF solution of NEM (10 mg/ml), and stirred an additional thirty minutes at room temperature. The mixture was then dialyzed twice against 0.05M phosphate buffer at pH 7.0.

b. Reaction of SMCC with ferritin:
Ferritin modified as above (5.0 mg/ml) was dialyzed into 0.05M $PO_4(Na+)$ pH 7.0. SMCC at 10 mg/ml, in dry DMF (used immediately after being made), was added to the ferritin, 20 $\mu$l per mg ferritin. The solution was stirred for 30 minutes at room temperature. The unreacted SMCC was removed by dialyzing the solution against 0.05M $PO_4(Na+)$. c. Conjugation of $\beta$-galactosidase and ferritin:

One hundred $\mu$l of maleimide coupled ferritin from above (5 mg/ml) was added, under $N_2$, to 3.5 ml of $\beta$-galactosidase (about 2 mg/ml). This gave a molar ratio of 1:15 (ferritin to $\beta$-galactosidase). $N_2$ was bubbled into the reaction tube for 10 minutes. The tube was sealed tightly and the reaction allowed to proceed 16–18 hours at room temperature. Cysteine, 100 $\mu$l of 10 mM in 0.05M $PO_4(Na+)$ pH 7.0, was added to the tube to react all remaining unconjugated maleimide groups. The reaction mixture was then chromatographed on a Biogel A5m column.

d. Modification of Albumin Sulphydryls with NEM:
Human albumin (300 mg) was dissolved in 3 ml of 0.05M $PO_4(Na+)$ pH 7.0. The albumin was dialyzed against 0.05M $PO_4(Na+)$ pH 7.0 overnight (vs. 3 l); 200 $\mu$l, at 100 mg/ml in dry DMF, was added to the albumin under $N_2$. The reaction mixture was stirred for 1 hour at room temperature. Excess NEM was removed by dialyzing against 0.05 M $PO_4(Na+)$ pH 7.0.

e. Coupling MBSE to NEM-modified Albumin:
To 300 mg of NEM-modified human albumin from above (about 75 mg/ml) was added 150 $\mu$l of MBSE at 100mg/ml in dry DMF giving a molar ratio of 13:1 (MBSE to albumin). The reaction mixture was stirred for 20 minutes at room temperature, and 0.2 volumes of 1.0M acetate (Na+) pH 5.0 was added to quench the reaction and preserve the maleimide groups. The unreacted maleimide was removed from the albumin by passing the reaction mixture over a G-10 column, 2.5 cm×20 cm, in 20 mM acetate (Na+), 1M NaCl pH 5.0. The void volume peak was collected and the albumin concentration measured spectrophotometrically at 280 nm. The modified albumin was tested for maleimide content and the remainder used for conjugatio as soon as possible.

f. Conjugation of Albumin with $\beta$-Galactosidase of the Ferritin Conjugate:

The ferritin conjugate of (c) above was dialyzed into 0.05M $PO_4(Na+)$, 0.5M NaCl, pH 7.0. The MBSE modified albumin (1 ml, at 10 mg/ml) from above was added to 5 ml of conjugate. $N_2$ was bubbled into the reaction tube for 10 minutes. The tube was tightly sealed, and the reaction was allowed to proceed 16–18 hours at room temperature. A molar excess of cysteine, 100 mM in 0.05M $PO_4(Na+)$ pH 7.0, to albumin was added to the reaction mixture to react all tne remaining unconjugated maleimide groups. The reaction mixture was then tested and/or chromatographed on Sepnarose CL-6B, as described below.

A portion of the ferritin conjugate mixtures were fractionated on a Biogel A5m column, 2.5 cm×90 cm. The column was equilibrated in 1×PBS, $N_3$, Mg, pH 6.8 (buffer was degassed). Up to 2 ml of conjugate mixture was applied to the column which was eluted in 1×PBS, $N_3$, Mg pH 6.8 (degassed), at 18 ml/hr. Fractions (5ml.) were collected.

Another portion of the ferritin conjugate mixtures were fractionated on a Sepharose CL-6B column, 1.5 cm×60 cm. The column was equilibrated in 1×PBS, $N_3$, Ng, pH 6.8 (degassed). Up to 0.75 ml of conjugate mixture was applied to the column, which was eluted in 1×PBS, $N_3$, Mg, pH 6.8 (degassed), at 10 ml/hr. Fractions (5ml) were collected.

g. Testing effects of serum on native enzyme activity with DUG (fluorogenic macromolecular substrate):
DUG was prepared as follows:
Ethyl umbelliferone 3-carboxylate was esterified according to the procedure of G. Schuman, H. Hansen, *Archiv der Pharmazie*, 271, 490 (1933). Next, a creased, 3-necked, 24/40 round bottomed flask was fitted with an overhead stirrer in the center neck, a nitrogen inlet with stopcock in the left neck, and a stopper in the right neck. HPLC grade $CH_3CN$ (380 ml) was added to the flask followed by the umbelliferone ester from above (18.31 g, 78.2 mmol). The mixture was heated to dissolve all the solid. Acetobromo-α-D-galactose (solid, 39.0 g, 89.7 mmol, Sigma Chemical Co.) was added all at once.

$Ag_2O$ (9.3 g, 80.0 mmol) was then added in spatula portions over a period of 5-10 minutes to the very vigorously stirred solution. When the additions were finished, the mixture was stirred an additional 30 minutes. Stirring was stopped, and the contents were allowed to settle for 2 hours.

The reaction mixture was filtered through a medium frit into a 500-ml suction flask. The filter cake was washed with two 15-ml portions of $CH_3CN$. The combined filtrates were concentrated to a heavy oil. The oil was taken up in 200 ml of $CH_2Cl_2$ and was washed in a 500-ml separatory funnel with two 50-ml portions of pH 7.0 sodium phosphate buffer (0.1M phosphate) chilled to 0°, followed by a 25-ml portion of saturated aqueous NaCl. The yellow solution was dried over $MgSO_4$ for 2 hours. Tne solution was then filtered and concentrated to a heavy oily foam.

To the oily foam was added 50-100 ml of absolute EtOH. The solid which formed was collected on a glass frit and washed with a 10-20-ml portion of EtOH chilled to 0°. The solid was then recrystallized from 225 ml of absolute EtOH to give, after washing with two 10-20-ml portions of EtOH chilled to −15° and drying on the filter and under vacuum, 30.56 g of fine needles. Concentration of the combined EtOH mother liquors (300–350 ml) to 200 ml yielded an additional 1.3 g of pure product.

A total of 31.86 g of tetraacetylgalactosylumbelliferone-3-carboxylic acid, ethyl ester was obtained (72.2%), m.p. 157°-158.5°.

The ester tetraacetate from above (28.22 g, 50 mmol, 250 meq of ester) was suspended in 250 ml of absolute EtOH in a 1000-ml round bottom flask under $N_2$. KOH (56 g of 85%, 850 mmol) was weighed into a 250 ml stoppered Erlenmeyer flask. Water (250 ml of deionized $H_2O$) was added to the KOH with swirling and cooling (ice bath). When solution was complete and its temperature had cooled to ~10°, the KOH solution was added to the stirring solution of the ester tetraacetate. Three 12-ml portions of $H_2O$ were used to rinse the KOH Erlenmeyer contents into the reaction flask. The reaction flask was covered by aluminum foil and left to stir overnight.

After 16 h the solution was very slightly turbid. Addition of ~10 ml of $H_2O$ caused clarification.

The solution was acidified with 70.8 ml of ice cold concentrated HCl added very slowly with cooling in an ice bath. The solution was concentrated to ~225-250 ml. A white solid precipitated and was collected in a large fritted glass funnel and washed with two portions of 1N HCl (15 ml at 0°) and 2 portions of $CH_3CN$ (30 ml). The solid was recrystallized from ~50 ml of near boiling $H_2O$ and the hot solution was filtered. On cooling to room temperature and then to 4° for 2 days a mass of white needles was obtained. These were collected on a glass fritted funnel, washed with 2×10 ml of ice cold 1N HCl and 2×20 ml of $CH_3CN$, and air-dried in the funnel to give 15.5 g (77%) of the galactosylumbelliferyl-3-carboxylic acid dihydrate. Concentration and recrystallization of the mother liquor gave an additional 480 mg of product.

Further purification was achieved by recrystallization once or twice from dry, HPLC grade $CH_3CN$. To 1.5 l of refluxing $CH_3CN$ was added 5 g of the acid dihydrate from above that had been dried under vacuum with heating. The mixture was heated near reflux until all the solid dissolved, usually about 4 minutes. The solution was filtered on a pre-heated Buchner funnel into a preheated 2 l. suction flask. The solution was allowed to cool to room temperature sealed from moisture. The flask was placed in the cold room overnight.

The resultant crystals were collected by filtration, washed with three 25-ml portions of $CH_3CN$, and placed under high vacuum to dry. This gave 4.7 g (94%) of galactosyl unbelliferone acid as an anhydrous hydroscopic white solid:

nmr: ($D_2O$) concentration dependent, δ8.7 (1,s,H4), 7.7 (1,d,H5), 7.17 (1 dd, H6) 7.05 (1,dd,H8), 5.27 (1,m,H1'), 3.8–4.35 (6,m,H2'–6')ppm.

uv: λmax=333 nm, $\epsilon$=11,200 (pH 8.75, phosphate buffer).

Anal. (Dihydrate): Calcd for $C_{16}H_{20}O_{12}$: C, 47.53; H, 4.99. Found: C, 47.51; H, 4.90.

Anal. (anhydrous): Calcd for $C_{16}H_{16}O_{10}$: C,52.18; H, 4.38. Found: C, 50.39; H, 4.86 (Calcd for 0.75 eq $H_2O$: C, 50.44; H, 4.61).

Aminodextran was prepared by dissolving dextran T40 (101 g) in 1.25M aqueous sodium chloroacetate (500 ml). A 2.5M aqueous solution of sodium hydroxide (500 ml) was added. The solution was heated at 80°-85° for 3 hr.

The reaction mixture was allowed to cool. Ethanol (1 l.) was added slowly to the stirred reaction mixture. The dextran began to precipitate after 350 ml had been added. Additional ethanol (2 l.) was added to ensure complete precipitation.

The precipitate separated as a gum. The supernatant was decanted easily. The dextran was purified by three additional precipitations. These were carried out in the following manner. The gum was dissolved in water (750 ml). Ethanol (3 l.) was then added slowly until a permanent cloudiness appeared in the solution, then more rapidly. The gummy precipitate of the dextran was then allowed to settle out overnight.

Carboxymethylated dextran T40 (as a gum, prepared from 100 g dextran T40) was dissolved in water (250 ml). A solution of N,N'-bis-(3-aminopropyl)piperazine (400 g, 2.0 mole) in hydrochloric acid (680 g of 8.52 mmole/g. 5.80 mole) was added. To the resulting solution was added EDCI (201 g, 1.05 mole) in water (250 ml). The reaction was stored at room temperature for 22 hrs. At the end of this period, ethanol (3 l.) was added. The dextran began to precipitate after 1.5 l. had been added. The precipitate was allowed to settle out overnight.

The aminodextran was purified by two additional precipitations. These were carried out as previously described. The final precipitation gave a milky suspension, which coagulated and settled out upon addition of a solution of lithium bromide (25 g) in ethanol (250 ml). The resulting gum was diluted in 1 l. and found to be 104 mM in amino groups by assay with trinitrobenzenesulfonic acid. A solution of the aminodextran (1 l. of 104 mM, 104 mmole) was treated with $K_2HPO_4$(89 g,0.5 mole) to give a solution buffered at pH 8–8.1.

The galactosyl umbelliferone acid from above (281 mg, 0.763 mmole) was weighed quickly into a pear-shaped flask containing a stir bar, and the flask was stoppered to protect the contents from atmospheric moisture. By means of a 10-ml syringe, 6 ml of DMF was added. The flask was stoppered and the mixture stirred to form a homogeneous suspension. EDCI (139.6 mg, 0.72 mmol) and NHS (87.9 mg, 0.764 mmol) were weighed and added to the stirring suspension. A bright yellow-orange solution resulted in the stoppered flask in two to five minutes. The flask was covered with aluminum foil and allowed to stir 2 h.

The aminodextran from above (53.78 g of solution) was weighed into a 250 ml, 3-necked, round-bottomed flask containing a football stir bar. The solution was brought to a pH of 8.3 (pH meter) by careful addition of concentrated NaOH. The electrode was rinsed into the flask to recover all the aminodextran.

To the vigorously stirring aminodextran solution was added dropwise from a 20 ml syringe the DMF solution of the galactosylumbelliferone acid NHS ester prepared above. The addition took 5-10 minutes. Three 0.5 ml portions of DMF were used to rinse the residual NHS ester from its reaction flask and the addition syringe into the aminodextran solution. The aminodextran flask was then stoppered, covered with aluminum foil, and allowed to stir 3 h.

The solution was then brought to a pH of 5.5 (pH meter) by careful addition of concentrated HCl. After acidification the product was precipitated by slow addition of 170 ml of 95% ethanol to the vigorously stirred solution. Precipitation began after 40 to 60 ml of ethanol had been added. The resultant gum was allowed to settle overnight at 4° in the stoppered flask covered by aluminum foil.

The supernatant was then decanted and discarded. The gum was rinsed with three 20-ml portions of 95% ethanol. The ethanol was drained as thoroughly as possible from the gum. To the crude product was added 10 ml of $H_2O$. The mixture was stirred and after about 1 h a clear, light brown, viscous liquid resulted. The liquid was transferred to Spectrapor® 1 dialysis bags. The bags were dialyzed into 4 liters of an aqueous solution containing 0.01M $NaH_2SO_4$ and 0.005M $NaN_3$. Buffer was changed at intervals of 4 to 48 h, and a total of 6 changes were made.

The contents of the bags were then centrifuged for 1 h at 16,000 rpm. The contents were carefully transferred to new tubes and centrifuged a second time. The clear supernatants were filtered through a 0.22 μm Millipore® filter. The product was analyzed and characterized, $\lambda_{max}$=342.5 nm (pH=7.0, 10 mM phosphate buffer), and then stored frozen in aliquots.

Fifty μl of serum or fifty μl of 1.75×PBS,$N_3$, Mg+0.5% RSA was mixed with 50 μl of β-galactosidase (approximately 20 ng/ml) and incubated for 2 h at room temperature, then 800 μl of 0.02M DUG in 1.75×PBS,$N_3$, Mg+0.1% RSA was added and the agents were mixed. Fluorescence rate was measured at 37° C., 10 second delay, 30 second read.

The results are summarzied below:

| Samples | ΔF/30 sec. | |
|---|---|---|
| | Buffer | Serum |
| β-galactosidase | 250 | 230 |
| β-galactosidase/ferritin | 325 | 260 | h. Inhibition of ferritin/β-galactosidase/albumin conjugate by anti-β-galactosidase:

To 50 μl of conjugate (50 ng/ml) prepared as above was added 50 μl of sheep anti-β-galactosidase at the following concentrations (as determined by the Ouchterlony Method): 1 ng/ml, 3 ng/ml, 10 ng/ml, 30 ng/ml, 100 ng/ml, 300 ng/μl and 1000 ng/μl. The mixture was incubated for 10 minutes at room temperature and 800 μl of 0.1 mM DUG (pH 7.0) was added. The fluorescence rate was measured at 37° C., 10 second delay, 30 second read (all reagents are made in 1.75×PBS, $N_3$, Mg+0.5% RSA).

The above procedure was repeated in the absence of anti-β-galactosidase.

For purposes of comparison the above procedures were repeated using a β-galactosidase/ferritin conjugate in place of the ferritin/β-galactosidase/albumin conjugate.

The results were calculated as follows:

$$\text{Residual Activity (\%)} = \frac{\Delta F_{30\ sec} + \text{Anti-}\beta\text{-galactosidase}}{\Delta F_{30\ sec} - \text{Anti-}\beta\text{-galactosidase}} \times 100$$

TABLE 1

| Anti-β-galactosidase concentration (ng/ml) | Residual Activity (%) | |
|---|---|---|
| | Ferritin/β-galactosidase/albumin* | β-galactosidase/ferritin |
| 1 | 100 | 100 |
| 3 | 100 | 98 |
| 10 | 98 | 95 |
| 30 | 89 | 78 |
| 100 | 69 | 55 |
| 300 | 40 | 32 |
| 1000 | 19 | 15 |

*Average of five runs.

The above data indicate that in a model system the ferritin/β-galactosidase/albumin conjugate is subject to less inhibition of activity of β-galactosidase in the presence of anti-β-galactosidase when compared to a β-galactosidase/ferritin conjugate.

i. Effect of serum on β-galactosidase activity with DUG. Comparison of β-galactosidase/ferritin conjugate and albumin/β-galactosidase/ferritin conjugate:

To 50 μl of serum sample or buffer was added 50 μl of either the β-galactosidase/ferritin conjugate (20–40 ng/ml) or the albumin/β-galactosidase/ferritin conjugate (20–40 ng/ml). 50 μl of 1% sodium dodecyl sulfate, Triton X-100 solution was added. The mixture was incubated 2 h, 37° C.; then 800 μl of 0.1 mM DUG (pH 7.0) was added. Fluorescence rate was measured at 37° C., 10 second delay, 30 second read.

The results were calculated as follows:

$$\text{Residual Activity (\%)} = \frac{\Delta F_{30\ sec} + \text{Serum}}{\Delta F_{30\ sec} + \text{Buffer}} \times 100$$

TABLE 2

| Serum Sample | Residual Activity (%) | |
|---|---|---|
| | β-Galactosidase/ferritin | Albumin/β-galactosidase/ferritin |
| A | 42.2 | 64.1 |
| B | 75.9 | 86.2 |
| C | 75.8 | 94.1 |
| D | 44.7 | 54.6 |
| E | 51.1 | 78.8 |
| F | 31.2 | 43.6 |
| G | 82.0 | 101.9 |
| H | 58.6 | 72.8 |

The above data indicate that a larger proportion of the β-galactosidase activity with DUG is retained when albumin is bound to the β-galactosidase of the conjugate.

What is claimed is:

1. In a method for the determination of the presence of an analyte in serum wherein the serum is combined with a receptor for a ligand and a conjugate of the ligand and an enzyme label and the amount of analyte is related to the amount of enzyme activity in said combination and wherein the serum contains endogenous components other than analyte which cause a diminution of the enzyme activity, the improvement which comprises binding said enzyme label to a label protectant wherein said label protectant is a compound selected from the group consisting of saccharides and animal derived plasma proteins having a molecular weight of about 20,000–100,000 and having an electronic charge similar to that of the conjugate of the ligand and the enzyme label.

2. The method of claim 1 wherein the analyte is a high molecular weight protein.

3. The method of claim 1 wherein the analyte is ferritin.

4. The method of claim 1 wherein the enzyme is β-galactosidase.

5. The method of claim 1 wherein the saccharides are selected from the group consisting of oligosaccharides, polysaccharides and mucopolysaccharides.

6. The method of claim 1 wherein the saccharide is a mucopolysaccharide.

7. The method of claim 1 wherein the animal derived protein is albumin.

8. A conjugate comprising
   (a) a ligand,
   (b) an enzyme label capable of providing a detectable signal in an immunoassay for determination of an analyte in a serum sample wherein the binding of the ligand to a receptor for ligand results in a modulation of the signal, and
   (c) a label protectant wherein said label protectant is a compound selected from the group consisting of saccharides and animal derived plasma proteins having a molecular weight of about 20,000–100,000 and an electronic charge similar to that of the conjugate of the ligand and the enzyme, said compound being bound to said enzyme label.

9. The conjugate of claim 8 wherein the ligand is ferritin.

10. The conjugate of claim 8 wherein the enzyme is β-galactosidase.

11. The conjugate of claim 8 wherein the saccharides are selected from the group consisting of oligosaccharides, polysaccharides and mucopolysacchardies.

12. The conjugate of claim 8 wherein the saccharide is a mucopolysaccharide.

13. The conjugate of claim 8 wherein the animal derived plasma protein is albumin.

14. A compound of the formula:

$$J_p(XY)_n(XZ)_m$$

wherein:
- J is a monoepitopic ligand or a polyepitopic ligand comprising polypeptides and proteins, polysaccharides, and aggregates thereof having a molecular weight of about 5,000 to about 5,000,000;
- X is a bond or a linking group of about 1 to 30 atoms comprising carbon, hydrogen, nitrogen, oxygen, and sulfur and the two Xs may be the same or different;
- Y is an enzyme label capable of producing a detectable signal in an enzyme immunoassay;
- p is a number between 1 and the molecular weight of Y divided by 2000, being 1 when n is greater than 1;
- n is a number between about 1 and about 10, being 1 when p is greater than 1;
- Z is a label protectant wherein said label protectant is a compound selected from the group consisting of saccharides, and animal derived plasma proteins having a molecular weight of about 20,000–100,000 daltons;
- m is a number of at least 1 per 40,000 molecular weight of Y.

15. The compound of claim 14 wherein Z is a saccharide selected from the group consisting of oligosaccharides, polysaccharides and mucopolysaccharides.

16. The compounds of claim 14 wherein Z is a mucopolysaccharide.

17. A compound of the formula:

$$J''\!-\![(CO)RWSY''S]_{n''}[WR(CO)\!-\!Z'']_{m'}$$

wherein:
- J" is a protein having a molecular weight of about 400,000–600,000 daltons;
- R is an aliphatic linking group of from 1 to 12 carbon atoms;
- W is derived from an activated olefin group, for reaction with a thiol group, having from 4 to 10 atoms comprising carbon, chalocogen of atomic number 8 to 16, and nitrogen;
- SY"S is β-galactosidase;
- n" is either 3 or 4;
- Z" is albumin; and
- m' is a number of at least 1 per SY"S.

18. The compound of claim 17 wherein W is α-succinimidyl.

19. The compound of claim 17 wherein J" is ferritin.

* * * * *